United States Patent
John

(10) Patent No.: US 8,312,057 B2
(45) Date of Patent: Nov. 13, 2012

(54) METHODS AND SYSTEM TO GENERATE DATA ASSOCIATED WITH A MEDICAL REPORT USING VOICE INPUTS

(75) Inventor: Joseph Chowalloor John, Bangalore (IN)

(73) Assignee: General Electric Company, Schenectady, NY (US)

( * ) Notice: Subject to any disclaimer, the term of this patent is extended or adjusted under 35 U.S.C. 154(b) by 1073 days.

(21) Appl. No.: 12/246,222

(22) Filed: Oct. 6, 2008

(65) Prior Publication Data

US 2010/0088095 A1    Apr. 8, 2010

(51) Int. Cl.
*G06F 17/30* (2006.01)

(52) U.S. Cl. ........ 707/804; 707/800; 707/811; 715/277; 715/201; 715/243; 704/9; 704/3; 705/2; 705/51

(58) Field of Classification Search ........... 707/999.104, 707/999.001–999.005, 804, 800, 811; 704/3, 704/9, 235, 275, 270; 715/277, 205, 201, 715/243, 209; 705/2, 51
See application file for complete search history.

(56) References Cited

U.S. PATENT DOCUMENTS

| | | | |
|---|---|---|---|
| 6,819,785 B1 * | 11/2004 | Vining et al. | 382/128 |
| 7,941,322 B2 * | 5/2011 | Shelton et al. | 705/2 |
| 2002/0188896 A1 * | 12/2002 | Filteau et al. | 714/57 |
| 2003/0144886 A1 * | 7/2003 | Taira | 705/3 |
| 2004/0243545 A1 * | 12/2004 | Boone et al. | 707/2 |
| 2006/0212452 A1 * | 9/2006 | Cornacchia, III | 707/10 |
| 2007/0106536 A1 * | 5/2007 | Moore | 705/3 |
| 2007/0106537 A1 * | 5/2007 | Moore | 705/3 |
| 2007/0116036 A1 * | 5/2007 | Moore | 370/462 |
| 2008/0021741 A1 * | 1/2008 | Holla et al. | 705/3 |
| 2008/0021834 A1 * | 1/2008 | Holla et al. | 705/51 |
| 2008/0040151 A1 * | 2/2008 | Moore | 705/2 |
| 2010/0324936 A1 * | 12/2010 | Vishnubhatla et al. | 705/3 |

* cited by examiner

*Primary Examiner* — Vijay B Chawan
(74) *Attorney, Agent, or Firm* — Hanley, Flight & Zimmerman, LLC

(57) ABSTRACT

Methods and system to generate data associated with a medical report using voice inputs are described herein. In one example implementation, a computer-implemented method to automatically generate data associated with a medical report using voice inputs received during a first encounter includes receiving a voice input from a source and determining an identity of the source. Additionally, the method includes performing a speech-to-text conversion on the voice input to generate a text string representing the voice input and associating the text string with the identity of the source. Further, the example method includes identifying and selecting one or more keywords from the text string. The one or more keywords are associated with one or more data fields. Further still, the method includes populating the one or more data fields with the identified keywords according to values associated with the identified keywords and the identity of the source.

31 Claims, 7 Drawing Sheets

METHODS AND SYSTEM TO GENERATE DATA ASSOCIATED WITH A MEDICAL REPORT USING VOICE INPUTS

BACKGROUND

Healthcare environments, such as hospitals and clinics, typically include information systems (e.g., hospital information systems (HIS), radiology information systems (RIS), storage systems, picture archiving and communication systems (PACS), electronic medical records (EMR)) to manage clinical information, management information, financial information, and/or scheduling information. The information may be centrally stored or divided into a plurality of locations. Healthcare practitioners may desire to access patient information at various points in a healthcare workflow. For example, during an encounter with a patient, medical personnel may access patient information, such as a patient's medical history and/or a patient's symptoms in an ongoing medical procedure. Alternatively, medical personal may enter new information, such as history, diagnostic, or treatment information, into a medical information system during an ongoing medical procedure.

Medical practitioners, such as doctors, surgeons, and other medical professionals, rely on clinical information stored in such systems during an encounter(s) with a patient to, for example, assess the condition of a patient, to provide immediate treatment in an emergency situation, to diagnose a patient and/or to provide any other medical treatment or attention. To generate this stored patient information, known systems require healthcare practitioners to spend a significant amount of time entering data into the system before, during and/or after an encounter with a patient. As a result, the efficiency of the healthcare practitioner is compromised. Additionally, such known systems are prone to incompleteness and/or inaccuracies because the data related to the patient encounter is typically entered by the healthcare practitioner after the encounter with the patient has occurred.

SUMMARY

In one example implementation, a computer-implemented method to automatically generate data associated with a medical report using voice inputs received during a first encounter includes receiving a voice input from a source and determining an identity of the source. Additionally, the method includes performing a speech-to-text conversion on the voice input to generate a text string representing the voice input and associating the text string with the identity of the source. Further, the example method includes identifying and selecting one or more keywords from the text string. The one or more keywords are associated with one or more data fields. Further still, the method includes populating the one or more data fields with the identified keywords according to values associated with the identified keywords and the identity of the source.

In another example implementation, a medical information system includes a data store in communication with one or more data entry systems to receive a voice input that includes information related to an encounter with a patient. Additionally, the example medical information system includes an identifier to identify a source of the voice input. The identifier is to associate the identity of the source with the voice input. Further, the example medical information system includes a converter to perform a speech-to-text conversion on the voice input to generate a text string representing the voice input and an analyzer to identify and select one or more keywords from the text string. The one or more keywords are associated with one or more data fields. Further still, the example medical information system includes a module to populate the one or more data fields with the identified keywords according to values associated with the identified keywords and the identity of the source.

Figure 1:
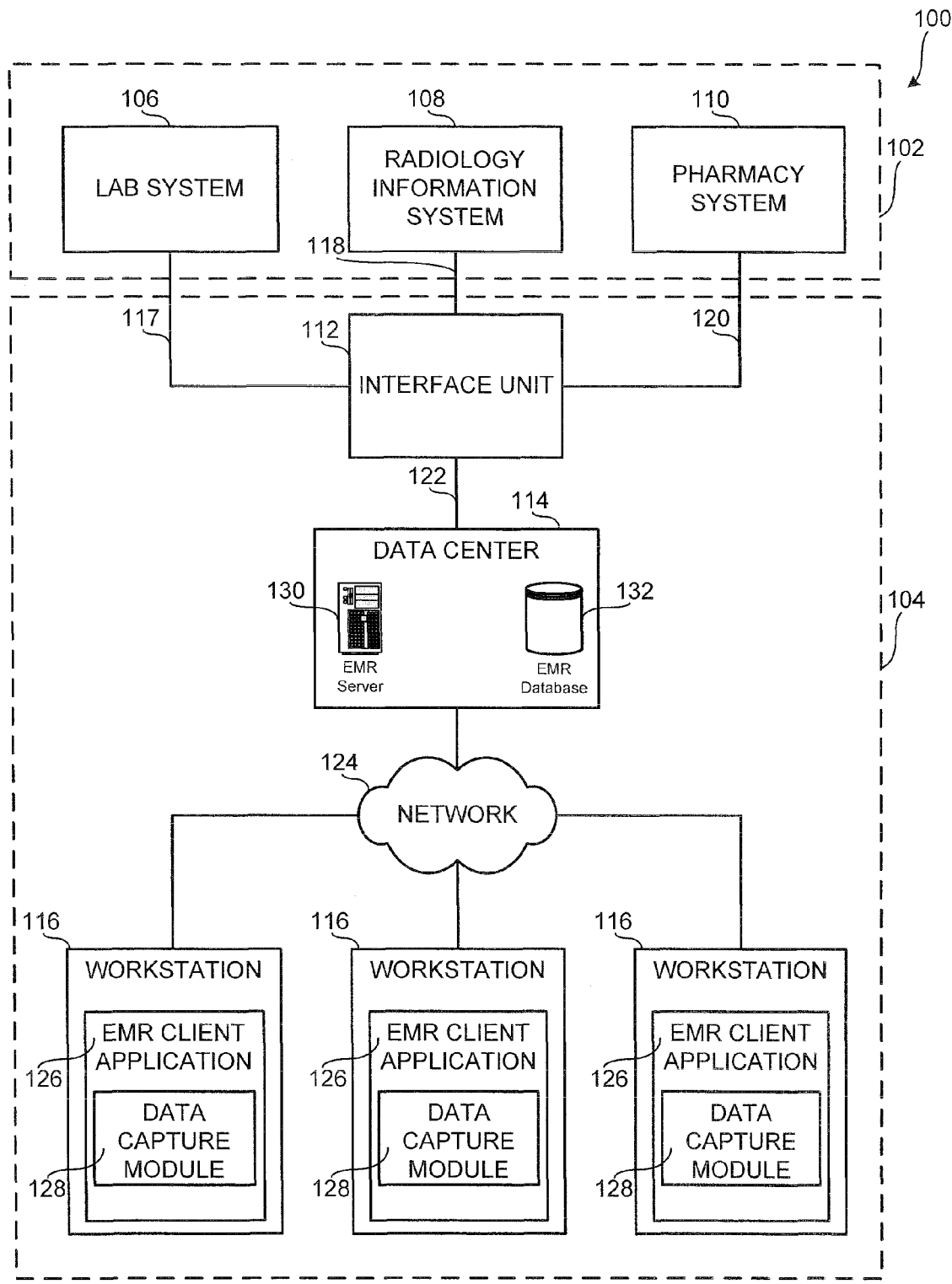
FIG. 1 is a block diagram of an example medical information system.

The foregoing summary, as well as the following detailed description of certain example implementations, will be better understood when read in conjunction with the appended drawings. For the purpose of illustrating the example methods and systems described herein, certain implementations are shown in the drawings. It should be understood, however, that the example methods and systems are not limited to the arrangements and instrumentality shown in the attached drawings.

DETAILED DESCRIPTION

Although the following discloses example methods, apparatus, systems, and articles of manufacture including, among other components, firmware and/or software executed on hardware, it should be noted that such methods, apparatus, systems and articles of manufacture are merely illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only way(s) to implement such methods, apparatus, systems, and/or articles of manufacture.

The example methods and systems described herein generate data associated with a medical report using voice inputs to advantageously enable healthcare practitioners to more quickly and efficiently generate, extract and/or record information related to a patient encounter to a patient medical report, record and/or history. In particular, the example methods and systems described herein enables healthcare practitioners to decrease the amount of data entry performed in association with a patient encounter while, at the same, increasing the accuracy and completeness of the corresponding medical reports. In addition, the example methods and systems described herein decrease the likelihood that critical information is missed or mistakenly overlooked during a patient encounter and, thus, the quality of delivered patient care is increased. Further, the example methods and systems described herein enables healthcare practitioners to review and/or revise the extracted and/or recorded information prior to and/or after this information is uploaded to the patient medical report, record and/or history. Further still, the example methods and systems described herein enables healthcare practitioners to advantageously utilize the generated and/or extracted data in clinical decision support.

FIG. 1 is a block diagram of an example medical information system 100 capable of implementing the example methods and apparatus described herein to generate data associated with a medical report using voice inputs. Specifically, the medical information system 100 includes an external interfacing system 102 and an electronics medical records system 104. The example external interfacing system 102 includes a lab system 106, a radiology information system 108, and a pharmacy system 110. The example electronics medical records system 104 includes an interface unit 112, a data center 114, and a plurality of workstations 116. In the illustrated example, the lab system 106, the radiology information system 108, and the pharmacy system 110 are housed in a healthcare facility and locally archived. However, in other implementations, the lab system 106, the radiology information system 108, and the pharmacy system 110 may be housed in one or more other suitable locations. Furthermore, one or more components of the medical information system 100 may be combined and/or implemented together. For example, the lab system 106 and/or the radiology information system 108 may be integrated with the pharmacy system 110; the radiology information system 108 may be integrated with the pharmacy system 110; and/or the three example information systems 106, 108 and/or 110 may be integrated together. In other example implementations, the medical information system 100 includes a subset of the illustrated information systems 106, 108 and/or 110. For example, the medical information system 100 may include only one or two of the lab system 106, the radiology information system 108, and the pharmacy system 110. Preferably, information (e.g., test results, observations, diagnosis, etc.) is entered into the lab system 106, the radiology information system 108, and the pharmacy system 110 by healthcare practitioners (e.g., radiologists, physicians, and/or technicians) before, during and/or after a patient examination and/or encounter.

The lab system 106 receives, stores and/or conveys medical information received from, for example, personnel at a hospital, clinic, and/or a physician's office associated with the Clinical Laboratory Department, which includes information related to Anatomic Pathology, Clinical Microbiology, Clinical Biochemistry, Hematology, etc. The radiology information system 108 stores information such as, for example, radiology reports, messages, warnings, alerts, patient scheduling information, patient demographic data, patient tracking information, and/or physician and patient status monitors. Additionally, the radiology information system 108 enables exam order entry (e.g., ordering an x-ray of a patient) and image and film tracking (e.g., tracking identities of one or more people that have checked out a film). In some examples, information in the radiology information system 108 is formatted according to the HL-7 (Health Level Seven) clinical communication protocol.

The pharmacy system 110 receives, stores and/or conveys medical information associated with orders for medications. In some examples, the pharmacy system 110 tracks medication orders to completion, generates medical bills associated with the medication dispensed, and monitors and/or controls the inventory in the pharmacy. The pharmacy system 110 interfaces with a number of other systems within the medical information system 100 to receive prescription orders and to generate medical bills associated with the dispensed medication such, for example, the electronic medical records system 104 and an insurance system (not shown). While the electronic medical records system 104 is depicted as separate from the external interfacing system 102 and the pharmacy system 110, in other examples, the electronic medical records system 104 may have an embedded pharmacy system 110.

The interface unit 112 includes a lab system interface 117, a radiology information system interface 118, a pharmacy system interface 120, and a data center interface connection 122. The interface unit 112 facilitates communication among the lab system 106, the radiology information system 108, the pharmacy system 110, and/or the data center 114. The interface connections 117, 118, 120, and 122 may be implemented by, for example, a Wide Area Network (WAN) such as a private network or the Internet. Accordingly, the interface unit 112 includes one or more communication components such as, for example, an Ethernet device, an asynchronous transfer mode (ATM) device, an 802.11 device, a DSL modem, a cable modem, a cellular modem, etc. In turn, the data center 114 communicates with the plurality of workstations 116 via a network 124, implemented at a plurality of locations (e.g., a hospital, clinic, doctor's office, other medical office, or terminal, etc.). The network 124 is implemented by, for example, the Internet, an intranet, a private network, a wired or wireless Local Area Network, and/or a wired or wireless Wide Area Network. In some examples, the interface unit 112 also includes a broker (e.g., a Mitra Imaging's PACS Broker) to allow medical information and medical images to be transmitted together and stored together.

In operation, the interface unit 112 receives images, medical reports, administrative information, and/or other clinical information from the information systems 106, 108, 110 via the interface connections 117, 118, 120. If necessary (e.g., when different formats of the received information are incompatible), the interface unit 112 translates or reformats (e.g., into Structured Query Language (SQL) or standard text) the medical information, such as medical reports, to be properly stored at the data center 114. Preferably, the reformatted medical information may be transmitted using a transmission protocol to enable different medical information to share common identification elements, such as a patient name or a social security number. Next, the interface unit 112 transmits the medical information to the data center 114 via the data center interface connection 122. Finally, medical information is stored in the data center 114.

The medical information is later viewable and easily retrievable at one or more of the workstations 116 (e.g., by their common identification element, such as a patient name or a record number). The workstations 116 may be any equipment (e.g., a personal computer) capable of executing software (e.g., a EMR client application 126) that permits electronic data (e.g., medical reports) and/or electronic medical images (e.g., x-rays, ultrasounds, MRI scans, etc.) to be acquired, stored, or transmitted for viewing and operation. The EMR client application 126 receives commands and/or other inputs from a user via, for example, a microphone, a keyboard, a mouse, a track ball, etc. Specifically, the workstations 116 receive a voice input(s) that relates to an encounter between a healthcare practitioner and a patient before, during and/or after the encounter. As shown in FIG. 1, the workstations 116 are connected to the network 124 and, thus, can communicate with each other, the data center 114, and/or any other device coupled to the network 124. As described in greater detail below in connection with FIGS. 4 and 5, the EMR client application 126 enables a healthcare practitioner to interact with the medical information system 100. For example, in response to a request from a physician, the user EMR client application 126 presents a patient medical history. Additionally, the EMR client application 126 includes one or more options related to the example methods and apparatus described herein to generate data associated with a medical report using voice inputs.

Additionally, the workstations 116 are provided with an example data capture module 128, such as a data capture plug-in or other software applet or program. The data capture module 128 of FIG. 1 generates and manages data associated with a medical report using voice inputs. Specifically, the data capture module 128 converts voice inputs using a speech-to-text conversion to generate a text string that represents the voice inputs. Thus, a healthcare practitioner (e.g., a physician) is able to generate a text string based on a conversation between, for example, the healthcare practitioner and a patient. Additionally, the data capture module 128 identifies keywords within the generated text string that are associated with one or more data fields such as, for example, a problem, an allergy or a medication. Advantageously, the example data capture module 128 enables the healthcare practitioner to more quickly and efficiently generate and/or record information related to a patient encounter to a patient medical report, record and/or history. Specifically, the data capture module 128 enables the healthcare practitioner to decrease the amount of data entry performed in association with a patient encounter. In addition, such an approach decreases the likelihood that critical information is missed or mistakenly overlooked. Further, the data capture module 128 enables the data center 114 to store the identified keywords in data fields within patient medical reports, records and/or histories according to the associated classification (e.g., a problem, an allergy or a medication) along with the text string. Such an approach increases the accuracy and completeness of medical reports, records and/or histories based on the patient encounter.

The example data center 114 of FIG. 1 is an archive to store information such as, for example, images, data, medical reports, and/or, more generally, patient medical records. In addition, the data center 114 may also serve as a central conduit to information located at other sources such as, for example, local archives, the lab systems, radiology information systems, and/or pharmacy systems (e.g., the lab system 106, the radiology information system 108, and the pharmacy system 110). That is, the data center 114 may store links or indicators (e.g., identification numbers, patient names, or record numbers) to information. In the illustrated example, the data center 114 is managed by an application server provider (ASP) and is located in a centralized location that may be accessed by a plurality of systems and facilities (e.g., hospitals, clinics, doctor's offices, other medical offices, and/or terminals). In some examples, the data center 114 may be spatially distant from the lab system 106, the radiology information system 108, and the pharmacy system 110 (e.g., at a General Electric® facility).

The example data center 114 of FIG. 1 includes an EMR server 130 and an EMR database 132. The EMR server 130 receives, processes, and conveys information to and from the components of the medical information system 100. Specifically, the EMR server 130 receives, processes, and conveys information to and from the different EMR client applications 126. The EMR database 132 stores the medical information described herein and provides access thereto.

Figure 2:
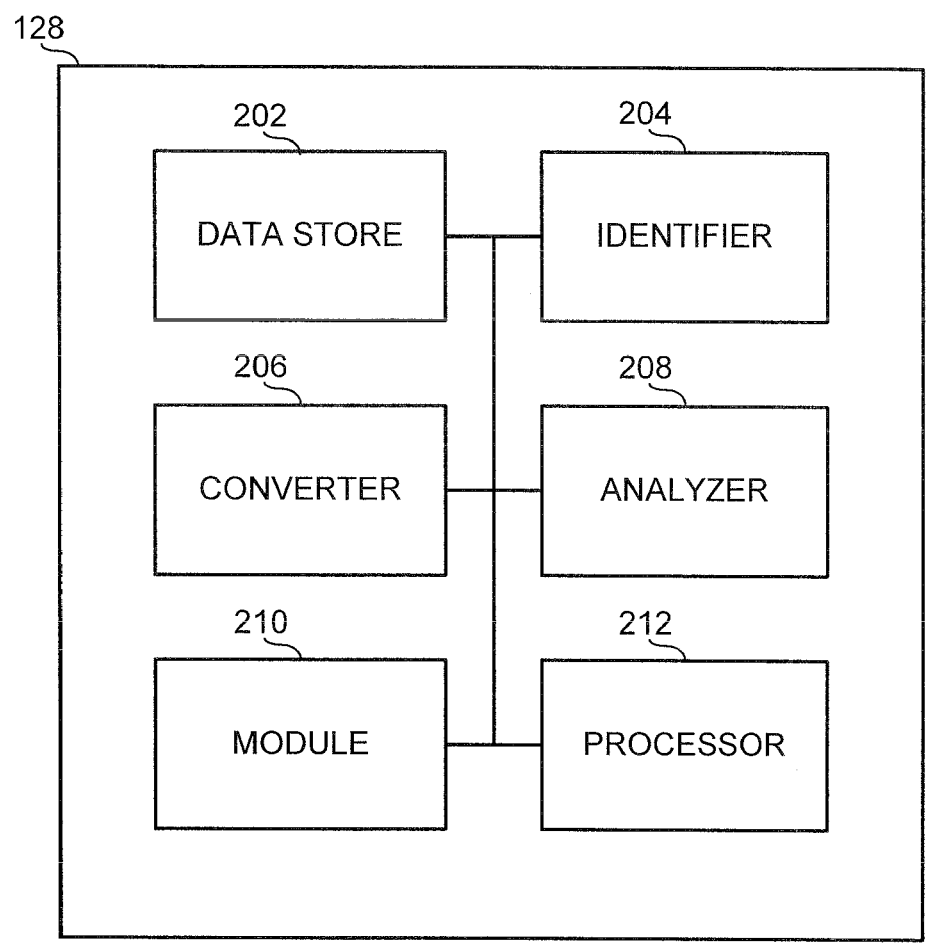
FIG. 2 is a block diagram of an example apparatus that may be used to implement the example data capture module of FIG. 1.

FIG. 2 is a block diagram of an example apparatus that may be used to implement the data capture module 128 of FIG. 1. In the illustrated example of FIG. 2, the example data capture module 128 includes a data store 202, an identifier 204, a converter 206, an analyzer 208, a module 210 and a processor 212. While an example manner of implementing the data capture module 128 of FIG. 1 has been illustrated in FIG. 2, one or more of the elements, processes and/or devices illustrated in FIG. 2 may be combined, divided, re-arranged, omitted, eliminated and/or implemented in any other way. Further, the data store 202, the identifier 204, the converter 206, the analyzer 208, the module 210, the processor 212 and/or, more generally, the example data capture module 128 of FIG. 2 may be implemented by hardware, software, firmware and/or any combination of hardware, software and/or firmware. Thus, for example, any of the data store 202, the identifier 204, the converter 206, the analyzer 208, the module 210, the processor 212 and/or, more generally, the example data capture module 128 of FIG. 2 can be implemented by one or more circuit(s), programmable processor(s), application specific integrated circuit(s) (ASIC(s)), programmable logic device(s) (PLD(s)) and/or field programmable logic device(s) (FPLD(s)), etc. When any of the appended claims are read to cover a purely software and/or firmware implementation, at least one of the data store 202, the identifier 204, the converter 206, the analyzer 208, the module 210, the processor 212 and/or, more generally, the example data capture module 128 of FIG. 2 are hereby expressly defined to include a tangible medium such as a memory, DVD, CD, etc., storing the software and/or firmware. Further still, the example data capture module 128 of FIG. 2 may include one or more elements, processes and/or devices in addition to, or instead of, those illustrated in FIG. 2, and/or may include more than one of any or all of the illustrated elements, processes and devices.

To generate data associated with a medical report(s) using voice input(s), the data capture module 128 initially conveys the received voice input(s) to the data store 202. The data store 202 creates a software object to represent the received voice input(s). The software object includes a plurality of properties that can be altered by, for example, the identifier 204, the converter 206, the analyzer 208, the module 210 and/or the processor 212. In some examples, the voice input is a recorded conversation between a healthcare practitioner and a patient during a patient encounter. In other examples, the voice input is a monologue given by the healthcare practitioner relating to an encounter with a patient. The data store 202 stores the voice input(s) and receives and stores the text string and the identified keywords as discussed below. Additionally, the data store 202 may receive and store any other data generated while processing the received voice input.

To identify the source or sources within the voice input(s), the processor 212 retrieves the voice input from the data store 202 and conveys the voice input to the identifier 204. The identifier 204 identifies the source of the voice input by comparing the frequency of the voice input to a known voice frequency such as, for example, the frequency of the healthcare practitioner's voice. The identifier 204 may also create a software object to represent the identified source or sources of the voice input. In practice, if the frequency of the voice input is substantially the same as the known voice frequency, the identifier 204 associates the voice input with a voice input from the healthcare practitioner by assigning a value to the voice input that is associated with the healthcare practitioner's voice. Alternatively, if the frequency of the voice input is different from the known voice frequency, the identifier 204 associates the voice input with a voice input from a patient by assigning a value to the voice input that is associated with the patient's voice.

If the voice input includes a conversation in which both the healthcare practitioner and the patient speak, the identifier 204 identifies intervals within the conversation that may each represent an interval of the voice input that is associated with the healthcare practitioner's voice and/or an interval of the voice input that is associated with the patient's voice. In this example, after the identifier 204 identifies the different intervals within the voice input, the frequency of each of the different intervals is compared to the known voice frequency to determine if the identifier 204 is to associate the interval of the voice input with the healthcare practitioner's voice or if the identifier 204 is to associate the interval of the voice input with the patient's voice. Once the identifier 204 has identified the source or sources (e.g., a healthcare practitioner and/or a patient) within the voice input, the voice input along with the associated values are retrieved by the processor 212 and conveyed to the data store 202 for storage.

To generate data associated with a medical report(s) by converting the voice input to a text string that represents the voice input, the processor 212 retrieves the voice input and the data generated by the identifier 204 from the data store 202 and conveys this information to the converter 206. Specifically, the converter 206 performs a speech-to-text conversion on the voice input and/or the different interval(s) within the voice input to generate a text string that represents the voice input and/or the different interval(s) within the voice input. The converter 206 may also create a software object to represent the text string. In some examples, the converter 206 compares a portion or portions of the voice input with known voice inputs that are associated with a known word, phrase and/or phrases. As the portion or portions of the voice input are identified as being substantially similar to the known word, phrase and/or phrases, the converter 206 generates a text string that represents the voice input. Additionally, the converter 206 associates the respective portion of the text string with the corresponding voice input and/or the different interval(s) within the voice input that may have been assigned a value by the identifier 204 that is associated with either the healthcare practitioner's voice or the patient's voice.

In some examples, the patient and/or the healthcare practitioner may not enunciate and/or articulate all of his or her words during the conversation that is associated with the voice input. As a result, the converter 206 may not be able to identify a portion or portions of the voice input. In this example, the converter 206 may suggest a known word, phase or phrases that is the most similar to the non-recognized portion of the voice input. Further, the converter 206 may assign a value to the suggested word, phrase or phrases to indicate that this portion of the text string was suggested by the converter 206. Once the converter 206 has performed the speech-to-text conversion on the voice input and/or on the different interval(s) within the voice input, the text string and the associated values are retrieved by the processor 212 and conveyed to the data store 202 for storage.

To extract data and/or identifiers from the text string (e.g., a plain text record), the processor 212 retrieves the text string and the associated values from the data store 202 and conveys them to the analyzer 208. In addition, data and/or identifiers may be extracted from electronic medical records (EMRs), optical character recognition (OCR), a medication order system, a database, a computerized physician order entry (CPOE), and/or any other suitable source. The analyzer 208 may also create a software object to represent the extracted data and/or identifiers from the text string. The analyzer 208 implements one or more algorithms capable of scanning the text string and identifying one or more keywords, phrases, abbreviations, instructions, etc. that are representative of a problem, an allergy, a medication, diagnosis, or any other relevant treatment information. The keywords, phrases, abbreviations and/or instructions may be any suitable terminology such as, for example, general medical terminology or specialized medical terminology that may be stored in the data store 202. In some examples, the keywords, phrases, abbreviations and/or instructions are associated with one or more data fields of a patient medical report. If the keywords, phrases, abbreviations, and/or instructions do not include a term or terminology that, for example, a healthcare practitioner may use within his or her practice field, the healthcare practitioner may add a new term and/or new terminology to the stored keywords, phrases, abbreviations and/or instructions by teaching the analyzer 208 the new term and/or new terminology to tailor the identified terms or terminology to the healthcare practitioner's particular practice field. Once the analyzer 208 has identified the keywords, phrases, abbreviations and/or instructions within the text string, the extracted data and/or identifiers and their associated values are retrieved by the processor 212 and conveyed to the data store 202 for storage.

The extracted representative data can then be used to populate one or more data fields of a medical report to summarize the keywords, phrases, abbreviations and/or instructions discussed during, for example, an encounter between the healthcare practitioner and the patient. In the illustrated example of FIG. 2, the processor 212 retrieves the extracted data and/or identifiers and their associated values from the data store 202 and conveys them to the module 210. The module 210 determines a classification of the extracted data based on the data field that the keywords, phrases, abbreviations and/or instructions are associated with, the identity of the source and the assigned values. Once the module 210 determines the classification of the extracted data, the module 210 populates the data fields with the corresponding identified keywords, phrases, abbreviations and/or instructions. For example, if a keyword is associated with a medication, the module 210 will populate a medication data field with the keyword. Alternatively, if the keyword is associated with a problem, the module 210 will populate a problem data field with the keyword.

Additionally, the module 210 may determine a classification of the extracted data based on the identity of the source (e.g., the healthcare practitioner or the patient) of the keyword. Specifically, in some examples, a keyword may be associated with either an allergy data field or a medication data field depending on whether the voice input is associated with the healthcare practitioner's voice or the patient's voice. For example, if a keyword (e.g., Penicillin) is associated with the patient's voice, the identified keyword may be associated with an allergy data field. However, if the keyword (e.g., Penicillin) is associated with the healthcare practitioner's voice, the identified keyword may be associated with a medication data field.

In practice, if the identifier 204 identifies that the voice input is associated with the patient's voice and the analyzer 208 identifies a keyword within the text string such as, for example, throat pain, the module 210 may classify the keyword as a problem and then populate a problem data field with the identified keyword. Alternatively, for example, if the identifier 204 identifies that the voice input is associated with the patient's voice and the analyzer 208 identifies a keyword within the text string such as, for example, aspirin, the module 210 may classify the keyword as an allergy, in part, because the keyword is associated with the patient's voice. The module 210 may then populate an allergy data field with the identified keyword. However, for example, if the identifier 204 identifies that the voice input is associated with the healthcare practitioner's voice and the analyzer 208 identifies a keyword within the text string such as, for example, Amoxicillin, the module 210 may classify the keyword as a medication, in part, because the keyword is associated with the healthcare practitioner's voice. The module 210 may then populate a medication data field with the identified keyword. The data capture module 128 then conveys the text string and the identified keywords, phrases, abbreviations and/or instructions (e.g., the software object(s) associated with the text string and the identified keywords, phrases, abbreviations and/or instructions), along with the associated values to the EMR database 132 for storage, where it can later be retrieved using one of the workstations 116 (FIG. 1). Thus, a healthcare practitioner is able to review the text string and the identified keywords, phrases, abbreviations and/or instructions to edit and/or verify the accuracy of this information, to save or upload this information to the patient medical report, record or history as, for example, discrete data, and/or to obtain the most relevant information desired by the healthcare practitioner.

Figure 3:
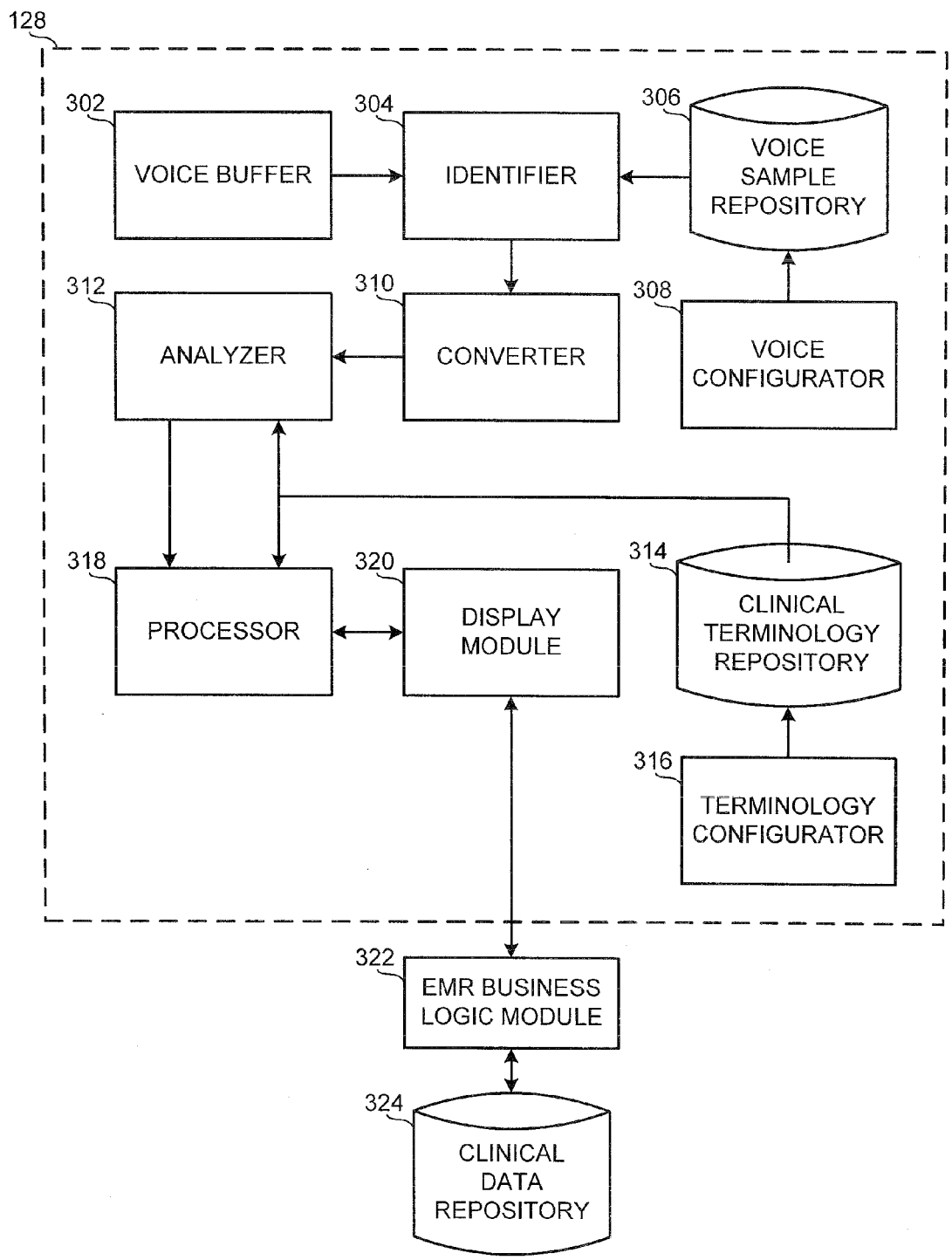
FIG. 3 is a detailed block diagram of another example apparatus that may be used to implement the example data capture module of FIG. 1.

FIG. 3 is a detailed block diagram of an example apparatus that may be used to implement the data capture module 128 of FIG. 1. In the illustrated example of FIG. 3, the example data capture module 128 includes a voice buffer 302, an identifier 304, a voice sample repository 306, a voice configurator 308, a converter 310, and an analyzer 312. Additionally, the example data capture module 128 includes a clinical terminology repository 314, a terminology configurator 316, a processor 318, a display module 320, an EMR business logic module 322 and a clinical data repository 324. The example apparatus of FIG. 3 may perform similar functions as the data store 202, the identifier 204, the converter 206, the analyzer 208, the module 210 and the processor 212 as described above in connection with FIG. 2. Specifically, the example apparatus of FIG. 3 generates data associated with a medical report using voice inputs.

In practice, the data capture module 128 initially conveys the received voice input(s) to the voice buffer 302, which may temporarily store the voice input(s) associated with an encounter between a healthcare practitioner and a patient. The voice buffer 302 may be at least partially used to implement the data store 202 of FIG. 2. The voice input(s) is then conveyed to the identifier 304, which identifies and determines if the voice input is associated with the healthcare practitioner's voice or the patient's voice. Specifically, the example apparatus is provided with the voice configurator 308 to train the example apparatus to identify the healthcare practitioner's voice. In particular, the healthcare practitioner utilizes the voice configurator 308 to generate voice samples that are stored in the voice sample repository 306. The voice input(s) is compared to the voice samples by the identifier 304 to identify the source of the voice input. Once the source of the voice input has been identified, the identifier 304 appends an identity tag to the voice input that is associated the source. The identifier 304 may be at least partially used to implement the identifier 204 of FIG. 2. The voice input(s) along with their associated identity tag(s) are then conveyed to the converter 310, which converts the voice input to a text string. Additionally, the converter 310 associates the identity tag from the voice input(s) with the respective text string. The converter 3 10 may be at least partially used to implement the converter 206 of FIG. 2.

The output from the converter 310 is then conveyed to the analyzer 312, which identifies keywords, phrases, abbreviations and/or instructions within the text string. Specifically, the terminology configurator 316 is provided to enable a healthcare practitioner to add and/or modify a clinical term, terminology, or vocabulary stored in the clinical terminology repository 314. The stored term, terminology, and/or vocabulary within the clinical terminology repository 314 is utilized by the analyzer 312 to identify the keywords, phrases, abbreviations and/or instructions within the text string. For example, the analyzer 312 may match the words "throat pain" within the text string with the words "throat pain" stored in the clinical terminology repository 314 and associated with a problem data field. Alternatively, the analyzer 312 may match the word "Amoxicillin" within the text string with the word "Amoxicillin" stored in the clinical terminology repository 314 and associated with a medication data field. Generally, the analyzer 312 receives inputs from the clinical terminology repository 314 to identify non-recognized portions of the text string (e.g., fine tune the text string) and to enable the analyzer 312 to identify the keywords, phrases, abbreviations and/or instructions within the text string. The analyzer 312 may be at least partially used to implement the analyzer 208 of FIG. 2.

The processor 318 processes, receives, obtains and/or conveys information between the different components of the data capture module 128. Additionally, the processor 318 may obtain the input from the analyzer 312 to suggest a known word, phase or phrases that is the most similar to the non-recognized portion of the text string. Specifically, the processor 318 attempts to match word(s) stored within the clinical terminology repository 314 with the non-recognized portion of the text string. The processor 318 may be at least partially used to implement the processor 212 and/or the converter 206 of FIG. 2.

Figure 5:
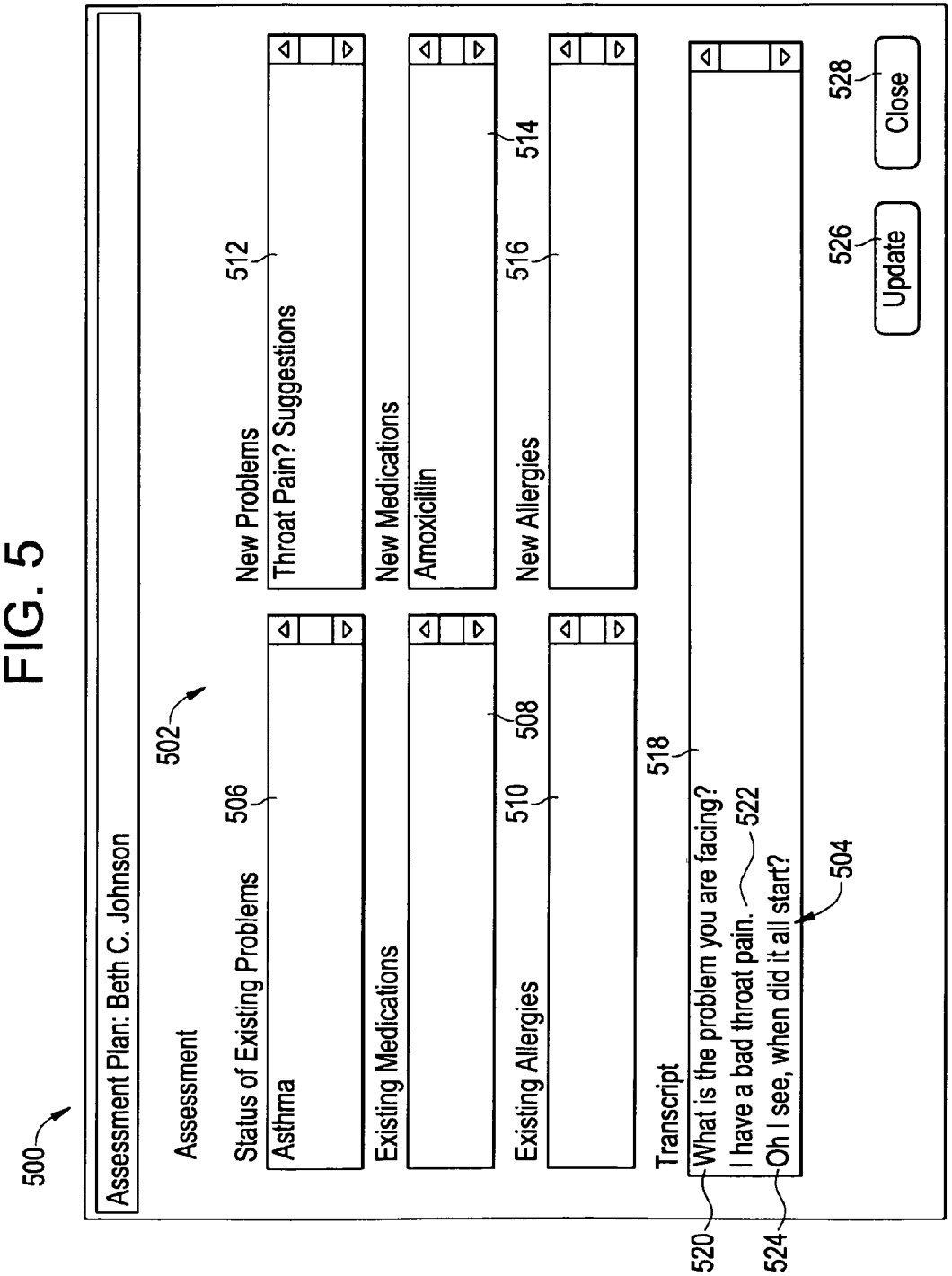
FIG. 5 is a screenshot of an example user interface used to convey the medical information stored and communicated in the example medical information system of FIG. 1.
Figure 6:
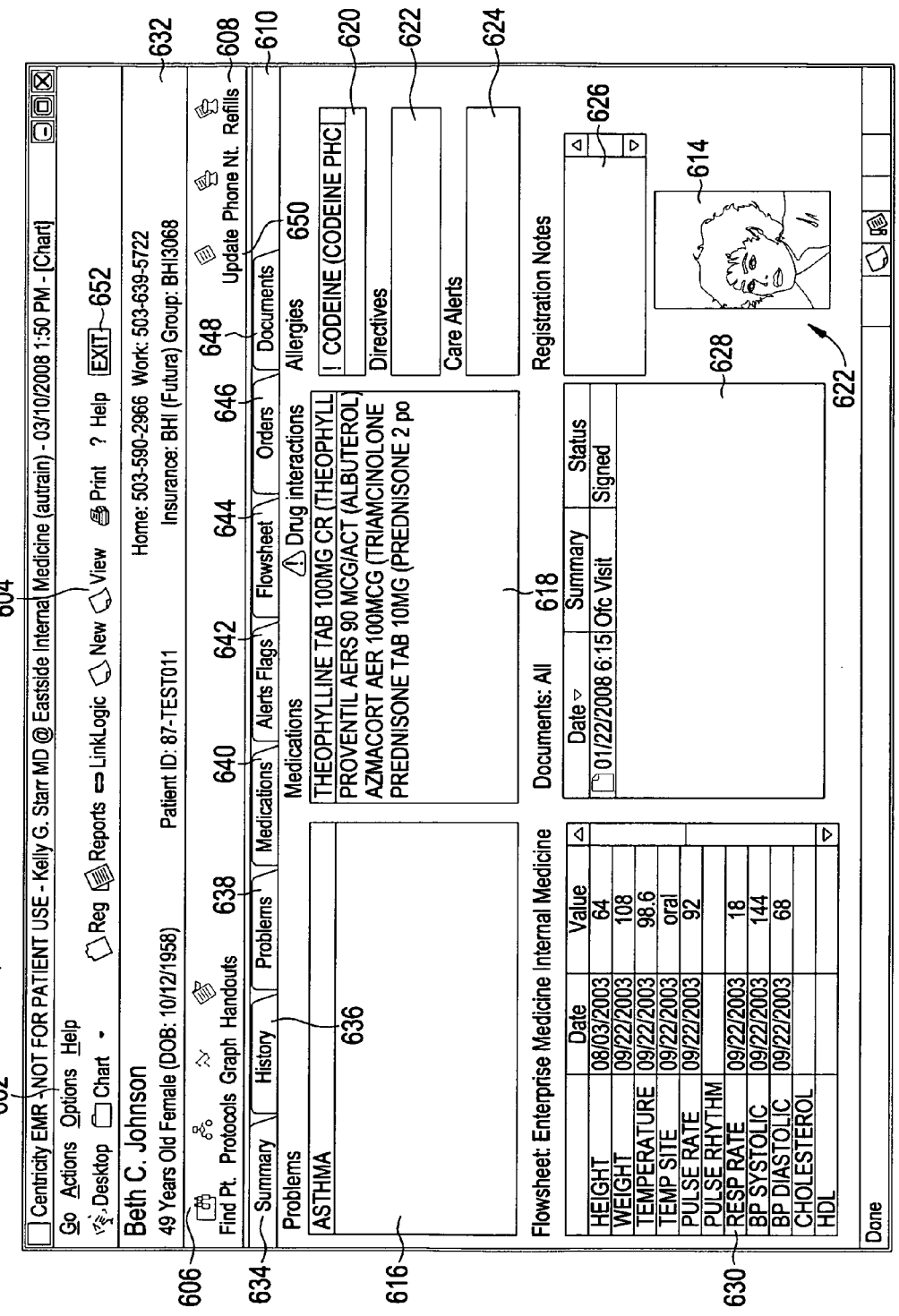
FIG. 6 is a screenshot of another example user interface used to convey the medical information stored and communicated in the example medical information system of FIG. 1.

The display module 320 displays the text string, the identified keywords, phrases, abbreviations and/or instructions to, for example, a healthcare practitioner using one of the workstations 116. In some examples, the display module 320 may be substantially similar to the screen shots as depicted in FIG. 5 or 6. The EMR business logic module 322 is provided with business logic to manage patient information such as, for example, demographics, medications, observations, allergies, problems, etc. Additionally, the business logic of the EMR business logic module 322 enables the EMR business logic module 322 to process transactions and store and retrieve data from the clinical data repository 324. The EMR business logic module 322 may be at least partially used to implement the module 210 of FIG. 2. The clinical data repository 324 is a real-time database that consolidates data from a variety of clinical sources that are associated with a particular patient and/or to facilitate the management of a specific clinical department. The data may be associated with clinical laboratory test results, patient demographics, pharmacy information, radiology reports and images, pathology reports, hospital admission/discharge/transfer dates, ICD-9 codes, discharges summaries, and/or progress notes.

Figure 4:
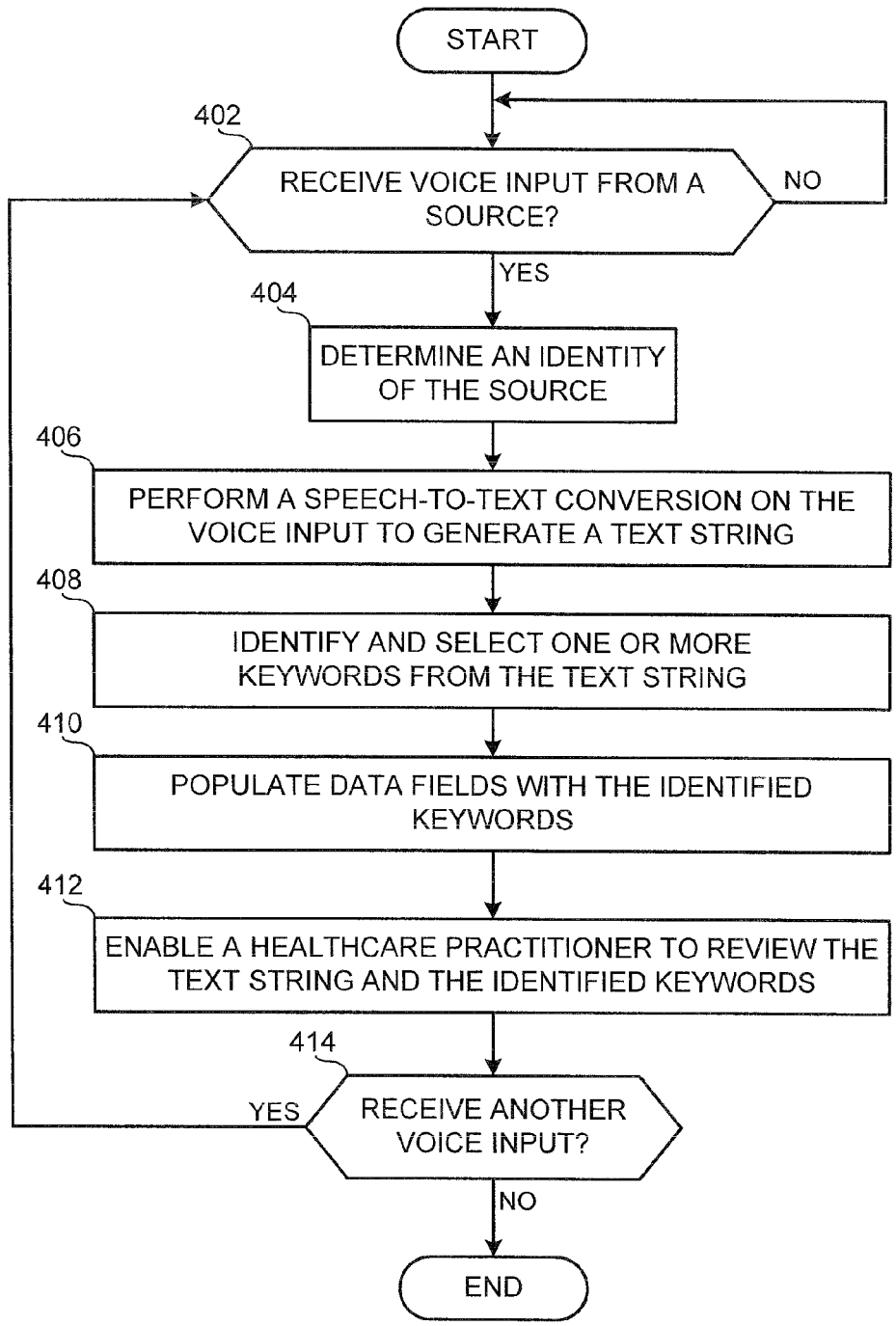
FIG. 4 is a flow diagram representative of example machine readable instructions that may be executed to implement the example data capture module of FIGS. 1 2 and/or 3.

The flow diagram depicted in FIG. 4 is representative of machine readable instructions that can be executed to implement the example methods and apparatus described herein. In particular, FIG. 4 depicts a flow diagram representative of machine readable instructions that may be executed to implement the example data capture module 128 of FIGS. 1 and/or 2 to generate data associated with a medical report using a voice input(s). The example processes of FIG. 4 may be performed using a processor, a controller and/or any other suitable processing device. For example, the example processes of FIG. 4 may be implemented in coded instructions stored on a tangible medium such as a flash memory, a read-only memory (ROM) and/or random-access memory (RAM) associated with a processor (e.g., an example processor system 700 discussed below in connection with FIG. 7). Alternatively, some or all of the example processes of FIG. 4 may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIG. 4 may be implemented manually or as any combination(s) of any of the foregoing techniques, for example, any combination of firmware, software, discrete logic and/or hardware. Further, although the example processes of FIG. 4 are described with reference to the flow diagram of FIG. 4, other methods of implementing the processes of FIG. 4 may be employed. For example, the order of execution of the blocks may be changed, and/or some of the blocks described may be changed, eliminated, sub-divided, or combined. Additionally, any or all of the example processes of FIG. 4 may be performed sequentially and/or in parallel by, for example, separate processing threads, processors, devices, discrete logic, circuits, etc.

Turning to FIG. 4, initially the data capture module 128 (FIGS. 1, 2 and 3) waits to receive a voice input that is associated with, for example, an encounter between a healthcare practitioner and a patient (block 402). The voice input is conveyed to the identifier 204 (FIG. 2) or 304 (FIG. 3), which identifies a source or sources (e.g., a healthcare practitioner and/or a patient) of the voice input (block 404) by, for example, comparing the frequency of the voice input to a known voice frequency or frequencies stored in, for example, the voice sample repository 306 (FIG. 3). Additionally, the identifier 204 (FIG. 2) or 304 (FIG. 3) may assign a value to the voice input or an interval within the voice input, which is associated with either the healthcare practitioner's voice or the patient's voice. The voice input along with the assigned values are then conveyed by the processor 212 (FIG. 2) to the converter 206 (FIG. 2) or 310 (FIG. 3), which coverts the voice input to a text string that represents the voice input (block 406). Additionally, the converter 206 (FIG. 2) or 310 (FIG. 3) associates the respective portion of the text string with the corresponding voice input and/or the different interval(s) within the voice input that may have been assigned a value by the identifier 204 (FIG. 2) or 304 (FIG. 3), which is associated with either the healthcare practitioner's voice or the patient's voice.

The text string along with the assigned values are then conveyed by the processor 212 (FIG. 2) or 318 (FIG. 3) to the analyzer 208 (FIG. 2) or 312 (FIG. 3), which identifies, selects and extracts information (e.g., via an OCR process) representative of keywords, phrases, abbreviations, instructions, etc. (block 408). As described above, the extracted information is used to populate different data fields of a patient medical report that may be associated with a problem, an allergy or a medication.

The extracted information is then conveyed by the processor 212 (FIG. 2) or 318 (FIG. 3) to the module 210 (FIG. 2) or the EMR business logic module 322 (FIG. 3). The module 210 (FIG. 2) or the EMR business logic module 322 (FIG. 3) determines the classification of the extracted data and then the module 210 (FIG. 2) or the EMR business logic module 322 (FIG. 3) populates the different data fields with the corresponding identified keywords, phrases, abbreviations and/or instructions (block 410).

The text string, the identified keywords (e.g., the software object associated with the text string and the identified keywords) and the associated values are then transmitted to the EMR server 130 (FIG. 1) and/or the EMR database 132 (FIG. 1) for storage. As described above, the workstations 116 (FIG. 1) have access to the EMR database 132 (FIG. 1), which enables a healthcare practitioner to be able to review and/or revise the text string and the identified keywords, phrases, abbreviations and/or instructions to edit and/or verify the accuracy of this information, to save or upload this information to the patient medical report, record or history stored on the EMR server 130 (FIG. 1) as, for example, discrete data, and/or the EMR database 132 (FIG. 1), and/or to obtain the most relevant information desired by a healthcare practitioner (block 412).

The example processes of FIG. 4 then determines whether it has received another voice input (block 414). Otherwise, the example processes of FIG. 4 are ended.

FIGS. 5 and 6 are screenshots of example user interfaces used to convey the medical information stored and communicated in the example medical information system 100 of FIG. 1.

FIG. 5 depicts an example user interface 500 that includes, among other things, a display area 502 for displaying a text string 504 and a plurality of data fields. In this example, the data fields correspond to a status of existing problems 506, existing medications 508, existing allergies 510, new problems 512, new medications 514, new allergies 516 and a transcript 518. However, other example user interfaces may be implemented having any other number of data fields (e.g., 1, 2, 3, 4, etc.) that correspond to any other topic.

The transcript 518 displays the text string 504, which has been generated from a voice input by the converter 206 (FIG. 2) or 310 (FIG. 3). As shown in the transcript 518, the text string has been divided into a first interval 520, a second interval 522 and a third interval 524 that is associated with either the healthcare practitioner's voice or the patient's voice. In some examples, the interval(s) associated with the healthcare practitioner's voice may be in a first color (e.g., black) and the interval(s) associated with the patient's voice may be in a second color (e.g., red). In this example, the first and third intervals 520 and 524 have been identified by the identifier 204 (FIG. 2) or 304 (FIG. 3) as being associated with a healthcare practitioner's voice and the second interval 522 has been identified by the identifier 204 (FIG. 2) or 304 (FIG. 3) as being associated with a patient's voice. In other examples (not shown), either the healthcare practitioner's name or the patient's name may appear adjacent the corresponding interval of the text string 504. Additionally, the user interface 500 also includes an update icon 526 and a close icon 528.

In practice, when a healthcare practitioner begins an encounter with a patient, the patient's electronic medical record is opened and the healthcare practitioner may review the data fields corresponding to the status of existing problems 506, the existing medications 508 and the existing allergies 510 that are associated with the particular patient. These data fields may display keywords, phrases, abbreviations and/or instructions identified and extracted from a text string generated from a previous voice input that is associated with a previous encounter between a healthcare practitioner and the particular patient. Once a conversation begins between the healthcare practitioner and the patient, the data capture module 128 (FIGS. 1 and 2) receives a voice input and the identifier 204 (FIG. 2) or 304 (FIG. 3) identifies the source or sources (e.g., the healthcare practitioner and/or the patient) of the voice input and the converter 206 (FIG. 2) or 310 (FIG. 3) then converts the voice input into a text string which is then displayed along with the identify of the source in the transcript 518. In this example, the identities of the sources are visually differentiated and/or represented by different colors. Next, the analyzer 208 (FIG. 2) or 312 (FIG. 3) analyzes the text string and identifies, selects and extracts keywords, phrases, abbreviations, instructions, etc. within the text string and the module 210 (FIG. 2) or the EMR business logic module 322 (FIG. 3) then determines a classification of the extracted data based on the data field that the extracted data is associated with, the identity of the source and the assigned values. The module 210 (FIG. 2) or the EMR business module logic 322 (FIG. 3) then populates the respective data fields with the corresponding identified keywords, phrases, abbreviations and/or instructions. In this example, the module 210 (FIG. 2) or the EMR business logic module 322 (FIG. 3) has identified the keyword throat pain that corresponds to the patient's voice and, thus, the module 210 (FIG. 2) or the EMR logic business module 322 (FIG. 3) populated the new problems 512 data field with the keyword throat pain.

Once the encounter between the healthcare practitioner and the patient has ended, the healthcare practitioner can review the display area 502 to verify the accuracy of the information and/or to revise (e.g., edit) the text string and/or the identified keywords, phrases, abbreviations and/or instructions by selecting on any of the data fields to change or add to the information displayed in the different data fields. After the healthcare practitioner has verified the accuracy of this information, the healthcare practitioner may select the update icon 526, which saves or uploads the information to the patient medical report, record or history stored on the EMR server 130 (FIG. 1) and/or the EMR database 132 (FIG. 1). After the information had been uploaded, the healthcare practitioner can select the close icon 528 to exit from the particular patient's electronic medical record.

FIG. 6 depicts an example user interface 600 that includes, among other things, tool bars 602, 604, 606, 608 and 610 which provide access to configuration menus, navigation tools, viewing tools, imaging applications, file management tools, etc. The tool bars 602, 604, 606, 608 and 610 may include additional icons and/or functionalities or less icons and/or functionalities than are shown in connection with the user interface 600.

The user interface 600 includes a display area 612 for displaying information related to a patient medical report and/or record and a patient identification image 614. Specifically, in this example, the display area 612 includes a plurality of data fields that correspond to problems 616, medications 618, allergies 620, directives 622, care alerts 624, registration notes 626, documents 628 and a flow sheet 630. However, other example user interfaces may be implemented having any other number of data fields (e.g., 1, 2, 3, 4, etc.) that correspond to any other topic. Additionally, the display area 612 includes a header 632 that may be associated with general patient information (e.g., name, birth date, contact information, and insurance information).

In practice, when a healthcare practitioner begins an encounter with a patient or wants to review or revise a patient's medical report or record, the patient's electronic medical record is opened and the healthcare practitioner may select a summary tab icon 634 to review the data fields associated with the problems 616, the medications 618, the allergies 620, the directives 622, the care alerts 624, the registration notes 626, the documents 628 and the flow sheet 630 that are each associated with the particular patient. However, the healthcare practitioner may select any of the other tab icons 636, 638, 640, 642, 644, 646 or 648 to review or revise different or more detailed information relating to the particular patient. After the healthcare practitioner has updated and/ or verified the information, the healthcare practitioner may select an update icon 650, which saves or uploads the information to the patient medical report, record or history stored on the EMR server 130 (FIG. 1) and/or the EMR database 132 (FIG. 1). After the information had been uploaded, the healthcare practitioner can select the exit icon 652 to exit from the particular patient's electronic medical record.

Figure 7:
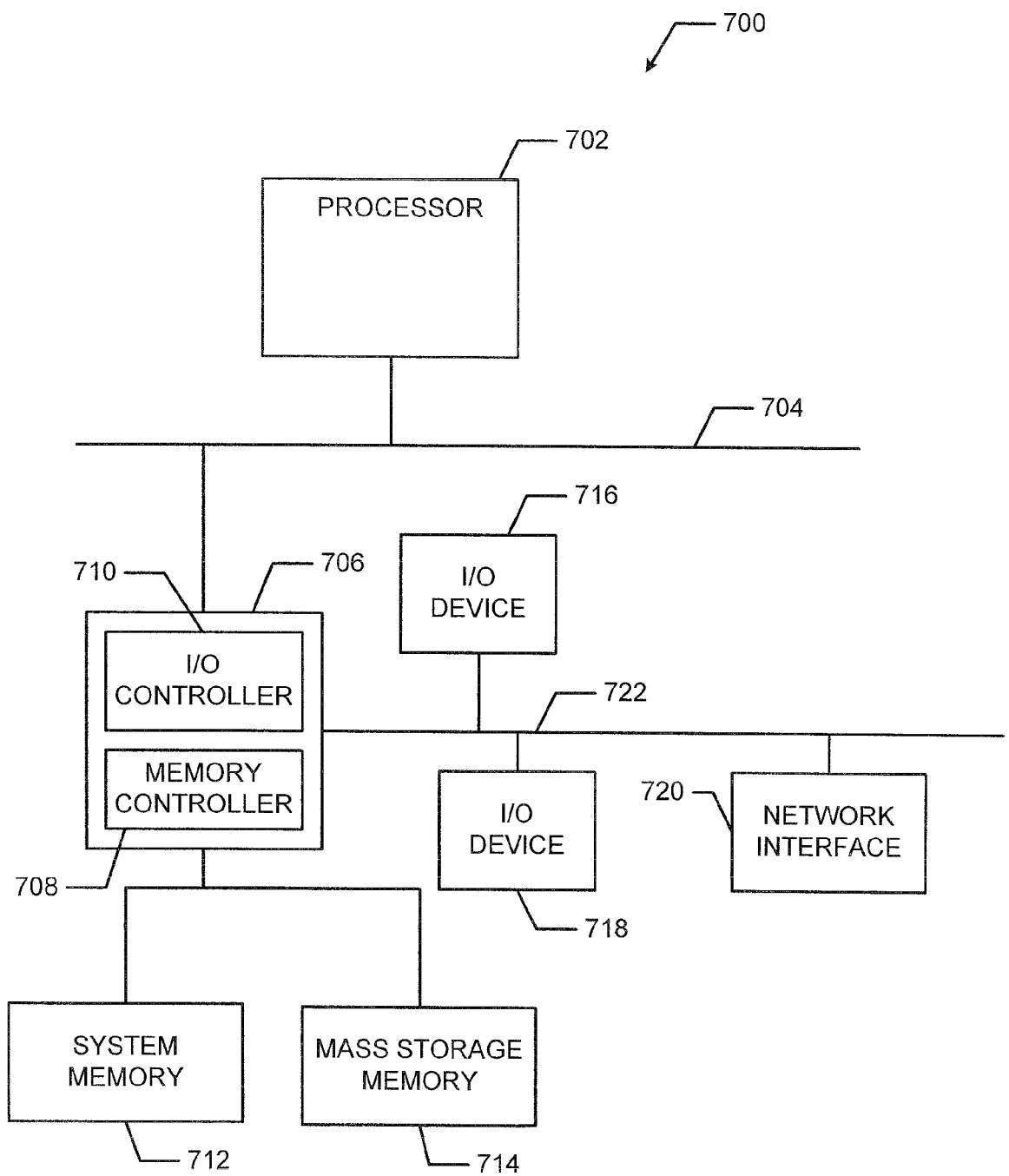
FIG. 7 is a block diagram of an example processor system that may be used to execute the machine readable instructions of FIG. 4 to implement the example data capture module of FIG. 2.

FIG. 7 is a block diagram of the example processor system 700 that may be used to implement the apparatus and methods described herein. As shown in FIG. 7, the processor system 700 includes a processor 702 that is coupled to an interconnection bus 704. The processor 702 may be any suitable processor, processing unit or microprocessor. Although not shown in FIG. 7, the processor system 700 may be a multi-processor system and, thus, may include one or more additional processors that are identical or similar to the processor 702 and that are communicatively coupled to the interconnection bus 704.

The processor 702 of FIG. 7 is coupled to a chipset 706, which includes a memory controller 708 and an input/output (I/O) controller 710. As is well known, a chipset typically provides I/O and memory management functions as well as a plurality of general purpose and/or special purpose registers, timers, etc. that are accessible or used by one or more processors coupled to the chipset 706. The memory controller 708 performs functions that enable the processor 702 (or processors if there are multiple processors) to access a system memory 712 and a mass storage memory 714.

The system memory 712 may include any desired type of volatile and/or non-volatile memory such as, for example, static random access memory (SRAM), dynamic random access memory (DRAM), flash memory, read-only memory (ROM), etc. The mass storage memory 714 may include any desired type of mass storage device including hard disk drives, optical drives, tape storage devices, etc.

The I/O controller 710 performs functions that enable the processor 702 to communicate with peripheral input/output (I/O) devices 716 and 718 and a network interface 720 via an I/O bus 722. The I/O devices 716 and 718 may be any desired type of I/O device such as, for example, a keyboard, a video display or monitor, a mouse, etc. The network interface 720 may be, for example, an Ethernet device, an asynchronous transfer mode (ATM) device, an 802.11 device, a DSL modem, a cable modem, a cellular modem, etc. that enables the processor system 700 to communicate with another processor system.

While the memory controller 708 and the I/O controller 710 are depicted in FIG. 7 as separate blocks within the chipset 706, the functions performed by these blocks may be integrated within a single semiconductor circuit or may be implemented using two or more separate integrated circuits.

Certain example implementations contemplate methods, systems and computer program products on any machine-readable media to implement functionality described above. Certain example implementations may be implemented using an existing computer processor, or by a special purpose computer processor incorporated for this or another purpose or by a hardwired and/or firmware system, for example.

Certain example implementations include computer-readable media for carrying or having computer-executable instructions or data structures stored thereon. Such computer-readable media may be any available media that may be accessed by a general purpose or special purpose computer or other machine with a processor. By way of example, such computer-readable media may include RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions include, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

The example methods and apparatus described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. The example methods and apparatus described herein may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Although certain methods, apparatus, and articles of manufacture have been described herein, the scope of coverage of this patent is not limited thereto. To the contrary, this patent covers all methods, apparatus, and articles of manufacture fairly falling within the scope of the appended claims either literally or under the doctrine of equivalents.

What is claimed is:

1. A computer-implemented method to automatically generate data associated with a medical report using voice inputs received during a first encounter, comprising:
    receiving a voice input from a source;
    determining an identity of the source;
    performing a speech-to-text conversion on the voice input to generate a text string representing the voice input;
    associating the text string with the identity of the source;
    automatically identifying and selecting one or more keywords from the text string, wherein the one or more keywords are associated with one or more data fields; and
    automatically populating the one or more data fields with the identified keywords according to values associated with the identified keywords and the identity of the source, the populated one or more data fields being different than the text string.

2. The method as defined in claim 1, wherein the voice input is associated with an interval.

3. The method as defined in claim 2, wherein determining the identity of the source comprises assigning a value to the interval and associating the value with the identity of the source.

4. The method as defined in claim 1, wherein populating the one or more data fields comprises extracting the identified keywords from the text string.

5. The method as defined in claim 1, further comprising enabling a healthcare practitioner to review the text string and the identified keywords.

6. The method as defined in claim 1, further comprising visually representing that the text string is associated with the identity of the source.

7. The method as defined in claim 1, wherein the source is associated with a healthcare practitioner.

8. The method as defined in claim 1, wherein the source is associated with a patient.

9. The method as defined in claim 1, wherein the one or more keywords are associated with general medical terminology or specialized medical terminology.

10. The method as defined in claim 1, wherein the one or more data fields are associated with at least one of a problem, an allergy, or a medication.

11. The method as defined in claim 1, further comprising enabling a healthcare practitioner to revise the one or more keywords to tailor the one or more keywords to a particular practice field.

12. The method as defined in claim 1, further comprising suggesting a recognized text string in place of a non-recognized portion of the voice input.

13. The method as defined in claim 1, further comprising enabling a healthcare practitioner to access the text string and the identified keywords during a second encounter.

14. The method as defined in claim 1, further comprising enabling a healthcare practitioner to edit at least one of the text string or the identified keywords.

15. The method as defined in claim 1, further comprising enabling a healthcare practitioner to save the text string and the identified keywords to the medical report.

16. The method as defined in claim 15, wherein the medical report is associated with a patient medical record.

17. A medical information system, comprising:
    a data store in communication with one or more data entry systems to receive a voice input that includes information related to an encounter with a patient;
    an identifier to identify a source of the voice input, wherein the identifier is to associate the identity of the source with the voice input;
    a converter to perform a speech-to-text conversion on the voice input to generate a text string representing the voice input;
    an analyzer to automatically identify and select one or more keywords from the text string, wherein the one or more keywords are associated with one or more data fields;
    a module to automatically populate the one or more data fields with the identified keywords according to values associated with the identified keywords and the identity of the source, the one or more data fields to be different than the text string.

18. The medical information system as defined in claim 17, further comprising one or more workstations in communication with the one or more data entry systems, wherein the workstations implement a user interface to enable a healthcare practitioner to review the text string and the identified keywords.

19. The medical information system as defined in claim 17, further comprising a data store in communication with the one or more data entry systems to receive and store the text string and the identified keywords, wherein the text string and the identified keywords are associated with a medical report.

20. The medical information system as defined in claim 17, wherein the identified keywords comprise one or more values associated with at least one of a problem, an allergy, or a medication.

21. The medical information system as defined in claim 17, wherein the one or more keywords are associated with at least one of general medical terminology or specialized medical terminology.

22. The medical information system as defined in claim 17, further comprising storage properties stored in association with a medical report, wherein the storage properties are based on at least some of the identified keywords.

23. A machine accessible medium having instructions stored thereon that, when executed, cause a machine to:
receive a voice input from a source during a first encounter;
determine an identity of the source;
perform a speech-to-text conversion on the voice input to generate a text string representing the voice input;
associate the text string with the identity of the source;
automatically identify and select one or more keywords from the text string, wherein the one or more keywords are associated with one or more data fields; and
automatically populate the one or more data fields with the identified keywords according to values associated with the identified keywords and the identity of the source, the populated one or more data fields to be different than the text string.

24. The machine accessible medium as defined in claim 23 having instructions stored there on that, when executed, cause the machine to associate the voice input with an interval.

25. The machine accessible medium as defined in claim 24 having instructions stored there on that, when executed, cause the machine to assign a value to the interval and associate the value with the identity of the source.

26. The machine accessible medium as defined in claim 23 having instructions stored there on that, when executed, cause the machine to enable a healthcare practitioner to review the text string and the identified keywords.

27. The machine accessible medium as defined in claim 23 having instructions stored there on that, when executed, cause the machine to visually represent that the text string is associated with the identity of the source.

28. The machine accessible medium as defined in claim 23 having instructions stored there on that, when executed, cause the machine to enable a healthcare practitioner to revise the one or more keywords to tailor the one or more keywords to a particular practice field.

29. The machine accessible medium as defined in claim 23 having instructions stored there on that, when executed, cause the machine to suggest a recognized text string in place of a non-recognized portion of the voice input.

30. The machine accessible medium as defined in claim 23 having instructions stored there on that, when executed, cause the machine to enable a healthcare practitioner to edit at least one of the text string or the identified keywords.

31. The machine accessible medium as defined in claim 23 having instructions stored there on that, when executed, cause the machine to enable a healthcare practitioner to save the text string and the identified keywords to a medical report.

* * * * *